United States Patent [19]

Rando et al.

[11] Patent Number: 5,593,835
[45] Date of Patent: Jan. 14, 1997

[54] METHODS AND KITS FOR RNA BINDING COMPOUNDS

[75] Inventors: Robert R. Rando, Newton Center; Yong Wang, Boston, both of Mass.

[73] Assignee: President and Fellows of Harvard College, Cambridge, Mass.

[21] Appl. No.: 440,084

[22] Filed: May 12, 1995

[51] Int. Cl.⁶ .................................................. C12Q 1/68
[52] U.S. Cl. .................................................. 435/6
[58] Field of Search ....................................... 435/6

[56] References Cited

U.S. PATENT DOCUMENTS 4,950,649   8/1990   Rinehart ..................... 514/10

OTHER PUBLICATIONS

LeGoffic et al. (1979) *Eur. J. Biochem.* 102:73–81.
Romaniuk et al. (1983) *Meth. Enzmol.* 100:52–59.
Tangy et al. (1983) *Eur. J. Biochem.* 131:581–587.
Cundliffe (1989) *Ann. Rev. Microbiol.* 43:207–233.
Jaeger et al. (1989) *Meth. Enzymol.* 183:281–306.
Milligan et al. (1989) *Meth. Enzymol.* 180:51–62.
Cundliffe et al., in *The Ribosome: Structure, Function & Evolution* (Schlessinger et al., eds. American Society for Microbiology, Washington, D.C. (1990) pp. 479–490.
Ellington et al. (1990) *Nature* 346:818–822.
Tuerk et al. (1990) *Science* 249:505–510.
von Ahsen et al. (1991) *Nature (London)* 353:368–370.
Woodcock et al. (1991) *EMBO J.* 10:3099–3103.
Beaudry et al. (1992) *Science* 257:635–641.
Bock et al. (1992) *Nature* 355:564–566.
Famulok et al. (1992) *J. Am. Chem. Soc.* 114:3990–3991.
Hutchin et al. (1993) *Nucleic Acids Res.* 21:4174–4179.
Zapp et al. (1993) *Cell* 74:969–978.
The American Medical Association (1993) *Aminoglycosides* 2(13), Chicago, IL, pp. 6:1–6:22.
Gait and Karn (1993) *Trends Biochem. Sci.* 18:255–259.
Kierzek et al. (1993) *J. Am. Chem. Soc.* 115:4985–4992.
Purohit et al. (1994) *Nature* 370:659–662.
Bevilacqua et al. (1994) *Biochem.* 33:11340–11348.
Lorsch et al. (1994) *Biochem.* 33:973–982.
Stage et al. (1995) *RNA* 1:95–101.

*Primary Examiner*—W. Gary Jones
*Assistant Examiner*—Ethan Whisenant
*Attorney, Agent, or Firm*—Lappin & Kusmer

[57] ABSTRACT

Disclosed are methods and kits for screening for compounds which bind to a target RNA, for isolating a target RNA from a sample, and for determining the presence and serum level of an aminoglycoside antibiotic in a subject. Also disclosed are kits for diagnosing the presence and identity of a bacterium or virus, and methods of increasing the potency of the binding interaction between an aminoglycoside antibiotic and a target RNA.

22 Claims, 7 Drawing Sheets

FIG. 1A  TOBRAMYCIN

FIG. 1B  AcTOBRAMYCIN

PyrTOBRAMYCIN (PYT)  FIG. 1C

FIG. 2

*Erythromycin A*

*Gentamycin $C_1$*

*Neomycin B*

METHODS AND KITS FOR RNA BINDING COMPOUNDS

FUNDING

This invention was made with Government support under Grants EY03624 and EY04096 awarded by the National Institutes of Health U.S. Public Health Service, and as such, the Government has certain rights in the invention.

FIELD OF THE INVENTION

This invention relates to the specific interaction of antibiotics with RNA. More specifically, this invention relates to methods and kits for identifying compounds which directly bind to specific RNAs, thereby interfering with RNA function.

BACKGROUND OF THE INVENTION

In certain situations, it may be desirable to inhibit the function of RNA and regulate its expression. For example, one method of treating bacterial or viral infections involves inhibiting the expression of bacterial or viral mRNA. Another method involves interfering with the ability of ribosomal RNA to take part in the mechanics of bacterial protein synthesis.

Certain classes of antibiotics are known to interact with RNA. For example, the antibiotic thiostreptone binds tightly to a 60mer from ribosomal RNA (Cundliffe et al., in *The Ribosome: Structure, Function & Evolution* (Schlessinger et al., eds.) American Society for Microbiology, Washington, D.C. (1990) pp. 479–490). Resistance to various antibiotics often involves methylation at specific rRNA sites (Cundliffe (1989) *Ann. Rev. Microbiol.* 43: 207–233). Aminoglycosidic aminocyclitol (aminoglycoside) antibiotics and peptide antibiotics are known to inhibit group I intron splicing by binding to specific regions of the RNA (von Ahsen et al. (1991) *Nature (London)* 353: 368–370). Some of these same aminoglycosides have also been found to inhibit hammerhead ribozyme function (Stage et al. (1995) *RNA* 1: 95–101). In addition, certain aminoglycosides and other protein synthesis inhibitors have been found to interact with specific bases in 16S rRNA (Woodcock et al. (1991) *EMBO J.* 10: 3099–3103). An oligonucleotide analog of the 16S rRNA has also been shown to interact with certain aminoglycosides (Purohit et al. (1994) *Nature* 370: 659–662). A molecular basis for hypersensitivity to aminoglycosides has been found to be located in a single base change in mitochondrial rRNA. (Hutchin et al. (1993) *Nucleic Acids Res.* 21: 4174–4179).

While these findings implicate RNA as the target for various antibiotics, there are few if any quantitative reports of the specific binding of any aminoglycoside directly to a particular domain of an RNA molecule.

Zapp et al. (*Cell* (1993) 74: 969–978) has demonstrated that neomycin B, lividomycin A, and tobramycin can block the binding of Rev, a viral regulatory protein required for viral gene expression, to its viral recognition element in the IIB (or RRE) region of HIV RNA. This blockage appears to be the result of competitive binding of the antibiotics to the RNA.

Thus, there is a need to elucidate the nature of the specific interaction between antibiotics and RNA which results in the inhibition of RNA function. There also remains a need for new antibiotics as well as other compounds which can effectively inhibit the function of specific RNAs with greater specificity and/or potency than existing antibiotics or compounds. A need for efficient methods of identifying these new compounds also exists.

SUMMARY OF THE INVENTION

It has been discovered that aminoglycosides can bind directly to specific regions of particular RNA molecules. It has here been discovered that the attachment of certain fluorescent moieties to an aminoglycoside antibiotic enables the subsequent binding interaction of the antibiotic with an RNA molecule to be enhanced. These findings have been exploited to develop the present invention, which includes quantitative screening methods and kits for RNA binding compounds, and methods of enhancing the antibiotic/RNA interaction, of isolating antibiotic-binding RNAs, and of quantitatively determining the serum level of an antibiotic.

In its first aspect, the invention provides a method of screening for compounds which bind to a target RNA. In an initial step of this method, the fluorescence of a fluorescently-labelled antibiotic is measured.

In some embodiments, the antibiotic is an aminoglycosid aminocyclitol (aminoglycoside) such as those from the tobramycin, neomycin, gentamicin, lividomycin, and streptomycin families, and derivatives thereof, which bind RNA. In other embodiments, the antibiotic belongs to the cycloheximide family. As used herein, the terms "tobramycin," "neomycin," "gentamicin," and "lividomycin," "streptomycin," and "cycloheximide" are meant to encompass those antibiotics in the tobramycin, neomycin, gentamicin, lividomycin, streptomycin, and cycloheximide families, respectively, and derivatives and analogs thereof, such as fluorescent analogs, which bind RNA.

The fluorescently-labelled antibiotic is bound to a preselected region of the target RNA, thereby forming a complex which is less fluorescent that the uncomplexed fluorescent antibiotic. In some embodiments, the fluorescently labelled antibiotic binds the target RNA with a dissociation constant ($K_D$) in the nanomolar to micromolar range. The complex is then mixed with a compound-to-be-tested, and the fluorescence of the antibiotic measured. The antibiotic becomes more fluorescent if the compound displaces the antibiotic in the complex and binds to the preselected region of the target RNA. In some embodiments, the fluorescence of the antibiotic is quenched when it binds the RNA, and is restored when the antibiotic is released from the complex by a competing compound.

In some embodiments the antibiotic is fluorescently labelled with pyrene, fluorescein, rhodamine, N,N-dimethylaminonapthylsulfonamide (DANSYL), 7-nitrobenzofurane, or derivatives thereof which can be covalently adhered to the antibiotic without interfering with its ability to bind RNA. As used herein, "pyrene" is meant to encompass fluorescent derivatives and analogs of pyrene. The fluorescent antibiotic may be adhered to a solid support such as a microtiter plate or affinity gel.

In preferred embodiments, the target RNA is a viral RNA such as HIV RNA, and the preselected region of HIV RNA comprises the RRE or TAR region. In other preferred embodiments, the target RNA is a decoding region of a bacterial ribosomal 16S RNA or a Gram-negative or Gram-positive bacterial RNA. In yet other embodiments, the target RNA comprises SEQ ID NO:8 or 9.

The invention also provides methods of screening for compounds which inhibit HIV replication. In this method, the TAR or RRE region of an HIV RNA is bound to the fluorescently-labelled antibiotic, the binding of this region inhibiting the replication of HIV.

A complex is formed when the antibiotic binds the TAR or RRE region of the RNA. This complex is either non-fluorescent or emits polarized fluorescence, in contrast to the uncomplexed antibiotic which emits unpolarized fluorescence or a less polarized fluorescence than the complex.

The complex is then mixed with a compound-to-be-tested. Fluorescence is then measured. The presence of fluorescence or an increase thereof is indicative of the displacement of the antibiotic from the complex and the binding of the compound to the RRE or TAR region of the HIV RNA. Alternatively, the polarization of the fluorescence is measured, a decrease in polarization being indicative of the displacement of the antibiotic in the complex and the binding of the compound to the TAR or RRE region of the target RNA.

In one preferred embodiment, the antibiotic is an aminoglycosidic aminocyclitol antibiotic. Some preferred aminoglycosides include tobramycin, gentamicin, neomycin, and derivatives thereof. In another preferred embodiment, the antibiotic is a member of the cycloheximide family and derivatives thereof, such as sparsomycin.

Another aspect of the invention is a method of isolating a target RNA from a sample, the target RNA comprising a known nucleic acid sequence which is bound by an aminoglycosidic aminocyclitol antibiotic. In this method, the antibiotic is adhered to a solid support, the antibiotic being fluorescently labelled and remaining fluorescent upon being bound to the support. The fluorescence of the adhered antibiotic is then measured. The adhered antibiotic is mixed with RNA isolated from the sample. Fluorescence is then measured fluorescence being reduced or quenched if the antibiotic binds to the target RNA.

In some preferred embodiments, the target RNA is a viral or bacterial RNA. In some embodiments, the target RNA is an HIV RNA, and the preselected region of HIV RNA comprises the RRE or TAR region. In other embodiments, the target RNA is a Gram-negative bacterial RNA or is a decoding region of bacterial ribosomal RNA. The invention also provides another method of screening for compounds which bind to a target RNA. In this method the polarization of light emitted from a fluorescently-labelled antibiotic is measured. The fluorescently-labelled antibiotic is bound to a preselected region of the target RNA, thereby forming a complex which emits light which is more polarized that light emitted from the uncomplexed fluorescent antibiotic. The complex is then mixed with a compound-to-be-tested, and the polarization of light emitted from the antibiotic measured, the emitted light being less polarized than light emitted from the complexed antibiotic if the compound displaces the antibiotic in the complex and binds to the preselected region of the target RNA.

In some preferred embodiments, the target RNA is a viral or bacterial RNA. In some embodiments, the target RNA is a decoding region of bacterial ribosomal RNA, an RNA from Gram-negative or Gram-positive bacteria, or the RRE or TAR region of HIV RNA.

In yet another aspect, the invention provides a kit for screening for compounds which bind a target bacterial or viral RNA. The kit comprises the target RNA and a fluorescently labelled antibiotic which has the ability to become reversibly non-fluorescent when specifically bound to a preselected region of the target RNA. In some preferred embodiments, the antibiotic is an aminoglycosidic aminocyclitol antibiotic or cycloheximide and derivatives thereof. In some embodiments, the antibiotic is fluorescently labelled with pyrene, fluorescein, rhodamine, N,N-dimethylaminonapthylsulfonamide (DANSYL), 7-nitrobenzofurane, or derivatives thereof which do not interfere with the binding of the antibiotic to RNA.

In another aspect, the invention provides a kit for screening for compounds which bind bacterial or viral RNA. The kit comprises a DNA which can be reverse transcribed to the target RNA, a reverse transcriptase, and a fluorescently labelled antibiotic which has the ability to become reversibly non-fluorescent when specifically bound to a preselected region of the target RNA.

The invention also provides a kit for diagnosing the presence and identity of a bacterium or virus. The kit comprises a plurality of fluorescently labelled antibiotics, each of which has the ability to specifically bind a different bacterial or viral RNA, and each fluorescently labelled antibiotic becoming non-fluorescent or emitting polarized light when bound to the RNA. In some preferred embodiments, the antibiotic is an aminoglycosidic aminocyclitol antibiotic such as tobramycin, gentamicin, or neomycin, or is cycloheximide or derivatives thereof. In some embodiments, the antibiotic is fluorescently labelled with pyrene, fluorescein, rhodamine, N,N-dimethylaminonapthylsulfonamide (DANSYL), 7-nitrobenzofurane or derivatives thereof. In other embodiments, the kit further comprises a solid support to which the antibiotic can be bound without loosing its fluorescence, or to which the bacterial RNA can be bound without loosing its ability to bind the antibiotic.

The invention also provides a kit for diagnosing the presence of HIV in a sample. This kit comprises a fluorescently labelled aminoglycoside antibiotic which binds a preselected region of HIV RNA, and a container for mixing RNA from the sample with the antibiotic. In some preferred embodiments, the preselected region of HIV RNA which is bound by the antibiotic comprises the RRE or TAR regions.

In another aspect, the invention provides a method of increasing the potency of the binding interaction between an aminoglycoside antibiotic and a target RNA. In this method, a pyrene or derivative thereof is covalently bound to the antibiotic before the antibiotic is bound to the RNA. In some embodiments, the aminoglycoside antibiotic is tobramycin or a derivative thereof.

A method for determining the serum level of an aminoglycoside antibiotic in a subject is also provided by the invention. In this method, a complex, comprising an RNA specifically bound to a labelled aminoglycoside antibiotic, is mixed with a serum sample obtained from the subject. The RNA in the complex contains a preselected region to which the antibiotic specifically binds. The antibiotic in the complex is covalently bound to a fluorescent label whose fluorescence is quenched when the antibiotic is complexed to the RNA. The level of antibiotic in the sample is then determined by comparing the fluorescence measured in the previous measuring step with the fluorescence emitted by the labelled antibiotic displaced from the complex after contact with a known amount of unlabelled antibiotic. The fluorescence of the labelled antibiotic is then measured, the labelled antibiotic becoming fluorescent if the serum sample contains a competing antibiotic which has displaced the labelled antibiotic in the complex and has specifically bound to the RNA.

In an alternative method of determining the presence and serum level of aminoglycoside antibiotic in a subjects the antibiotic is covalently bound to a fluorescent label which emits polarized light when the antibiotic is complexed to the RNA. The fluorescence of the labelled antibiotic is then measured, the labelled antibiotic emitting unpolarized light if the serum sample contains a competing antibiotic which has displaced the labelled antibiotic in the complex and has specifically bound to the RNA.

In some preferred embodiments, the RNA in the complex is a bacterial or viral RNA. In specific embodiments, the RNA is an HIV RNA comprising the RRE or TAR regions. In other preferred embodiments, the RNA is a decoding region of a bacterial rRNA, or is a Gram-negative or Gram-positive bacterial RNA. In yet other preferred embodiments, the RNA comprises SEQ ID NO:8 or 9. In some embodiments, the fluorescent label is pyrene or a derivative thereof, and/or the aminoglycoside antibiotic is tobramycin, neomycin, gentamicin, or derivatives thereof.

In another aspect, the invention provides a kit for determining the presence and serum level of an aminoglycoside antibiotic in a subject. The kit includes (1) an RNA which is specifically bound by the antibiotic, (2) the antibiotic which has been fluorescently labelled with a label whose fluorescence is quenched when the labelled antibiotic specifically binds the RNA, and (3) the antibiotic in unlabelled and uncomplexed form with which is prepared a standard fluorescence curve.

BRIEF DESCRIPTION OF THE DRAWINGS

The foregoing and other objects of the present invention, the various features thereof, as well as the invention itself may be more fully understood from the following description, when read together with the accompanying drawings in which.

DETAILED DESCRIPTION OF THE PREFERRED EMBODIMENTS

The patent and scientific literature referred to herein establishes the knowledge that is available to those with skill in the art. The issued U.S. patents, allowed applications, published foreign applications, and references cited herein are hereby incorporated by reference.

The present invention provides methods of screening for, or identifying, antibiotics and other compounds which bind to a specific region of a target RNA. This invention is based on the finding that some antibiotics such as, but not limited to, aminoglycosides, interact directly with specific regions of RNA, and by doing so, interfere with the function of that RNA.

The target RNA can be any RNA to which a known antibiotic binds at a preselected region. RNAs often targeted include rRNAs and mRNAs, but any RNA can be targeted. Representative RNAs are from organisms which infect animals, including bacteria (such as Gram-negative or Gram-positive bacteria) and viruses (such as HIV, herpes, influenza, etc.). Regions of the target RNA selected for binding to the antibiotic include those sequences or conformations known to be bound by a particular antibiotic. For example, the TAR region and the RRE region of HIV RNA are bound tightly and selectively by tobramycin and its derivatives, as described below. The decoding regions of various rRNAs such as a 16S rRNA are bound by tobramycin, kanamycins A, B, and C, and neomycin (LeGoffic et al. (1979) *Eur. J. Biochem.* 102: 73–81. Gram-negative bacterial RNAs, for example, those from *E. coli*, are bound by the aminoglycosides tobramycin, neomycin, streptomycin, and gentamicin, and splicing regions of bacterial RNA are also recognized and bound by tobramycin, neomycin, streptomycin, and gentamicin.

Particular representative RNAs known to be bound by aminoglycoside antibiotics include a nucleotide sequence set forth in the Sequence Listing as SEQ ID NO:8 or 9.

In the methods of the invention, the fluorescence or light emitted from a fluorescently-labelled antibiotic is measured. The label may be any fluorescent label or fluorophore that does not interfere with the ability of the antibiotic to bind to the preselected region of the RNA. Particularly useful fluorescent labels include those whose fluorescence is reduced or quenched when the labelled antibiotic binds the RNA. Other useful fluorophores include those which emit light that is polarized (or more polarized) when the antibiotic is bound to the RNA than when the antibiotic is uncomplexed. Some representative labels include pyrene, fluorescein, rhodamine, N,N-dimethylaminonapthylsulfonamide (DANSYL), 7-nitrobenzofurane, and derivatives of these labels which can be covalently adhered to the antibiotic without interfering with the ability of the antibiotic to bind RNA. The fluorescent labels are covalently bound or linked to the antibiotic directly or indirectly by any method known in the art, one of which is described in the exemplification, below. For example, a linker of either acetyl or butyryl can be used to link the label to the antibiotic. Other useful linkers include aliphatic acids (e.g., hexanoyl and dexanoyl), peptides no more than five amino acids in length, and water soluble linkers such as the ethylene glycols.

The antibiotic to which the fluorescent label is bound can be any antibiotic which is known to bind a particular region of a specific RNA. That region is preselected before the commencement of the first step of the method and is used as a measure of degree of complexing by which other compounds are later compared to the antibiotic.

Some particularly useful antibiotics include aminoglycosidic aminocyclitols or "aminoglycosides" having a six-membered aminocyclitol ring to which are attached by glycosidic linkages a variety of amino- and nonamino-containing sugars. Aminoglycosides have similar antibacterial spectra and pharmacokinetic properties.

That aminoglycosides can directly interact with RNA is consistent with the chemistries involved. The aminoglycosides are polycationic saccharides at neutral pH's and likely to interact effectively with RNA both through electrostatic interactions and through hydrogen bonding.

Figure 1A:
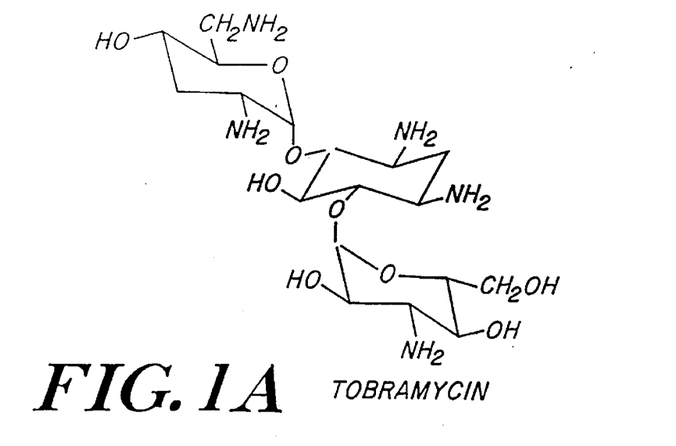
FIG. 1A is a diagrammatic representation of the structure of tobramycin.
Figure 1B:
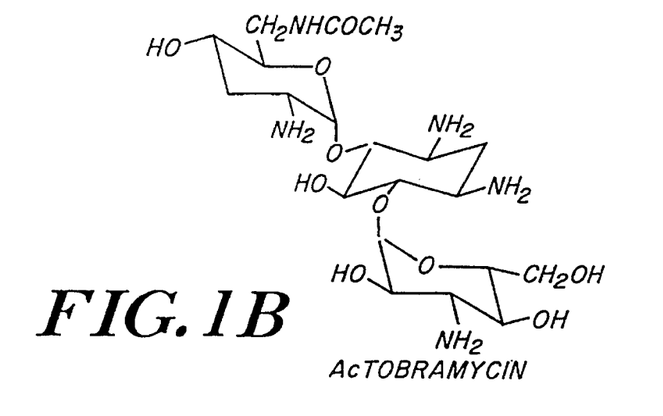
FIG. 1B is a diagrammatic representation of the tobramycin derivative 6'-N-acetyl tobramycin (acetylbramycin)
Figure 1C:
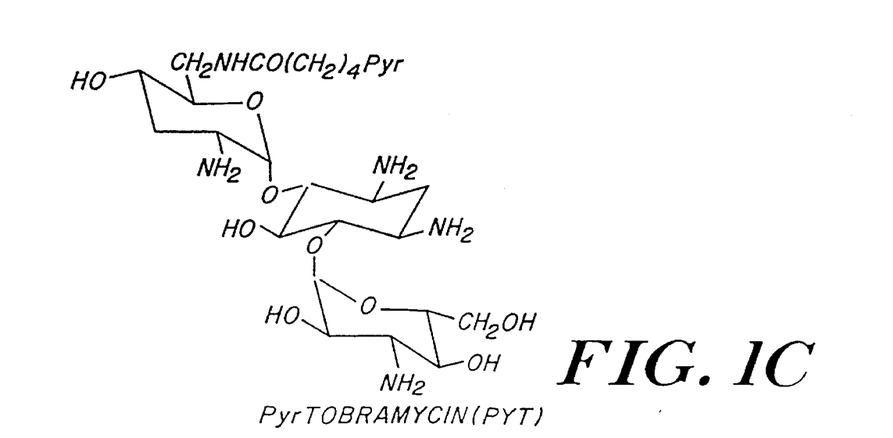
FIG. 1C is a diagrammatic representation of the tobramycin derivative 6'-D-4-pyrene-butyryl tobramycin (pyrotobramycin)

Particularly useful examples of aminoglycosides include those which are part of one of the following families: tobramycin (FIG. 1A), gentamicin (FIG. 2B), neomycin (FIG. 2C), and fluorescent analogs and other derivatives of these antibiotics (e.g. acetyl or pyrenebutyryl analogs such as actylbramycin (FIG. 1B), and 6'-N4pyrenebutyryl tobramycin (FIG. 1C). Other aminoglycosides such as streptomycin, paromycin, kanamycin, amakacin, sisomicin, lividomycin, and netilmicin are also useful (see, The American Medical Association (1993) *Aminoglycosides* 2 (13), Chicago, Ill., pp. 6:1–6:22, for a review).

Other particularly useful antibiotics are those which are members of the cycloheximide family, including but not limited to cycloheximide, sparsomycin, and analogs and fluorescent derivatives thereof. These antibiotics may be isolated from their natural source by methods known in the art, or may be commercially available from many sources, including Fluka (Ronkonkoma, N.Y.) and Sigma Chemical Co. (St. Louis, Mo.).

Figure 2:
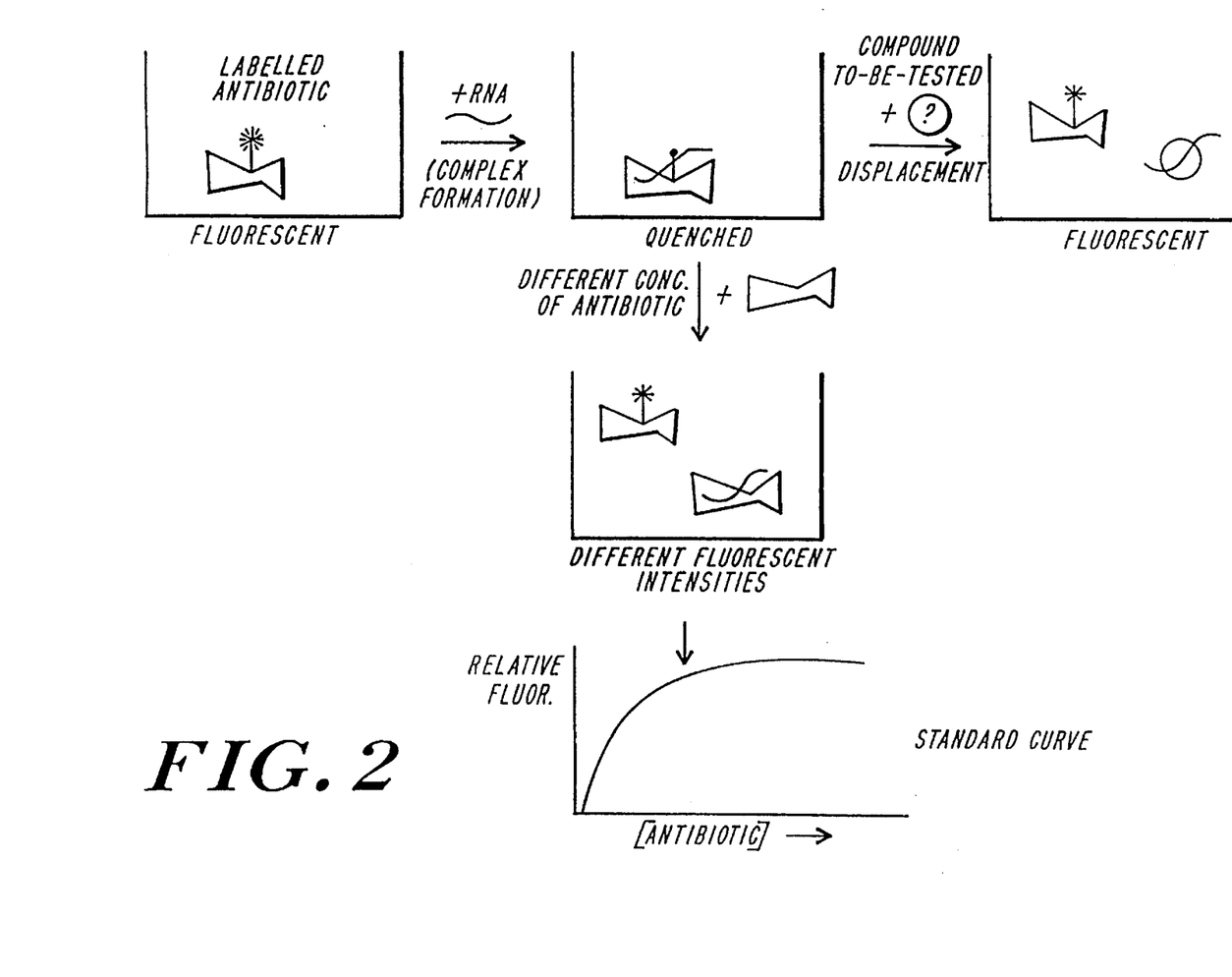
FIG. 2 is a diagrammatic representation of the method of screening for compounds which bind to a target RNA.
Figure 3A:
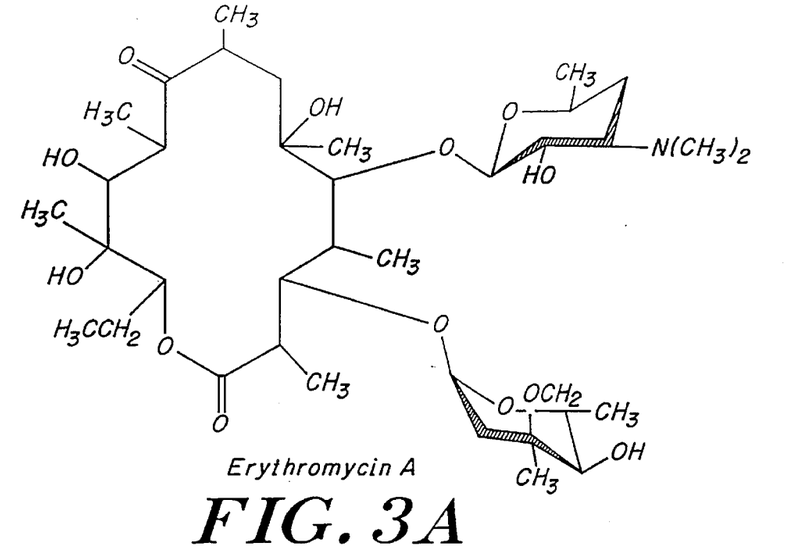
FIG. 3A is a diagrammatic representation of the antibiotic erythromycin A.
Figure 3B:
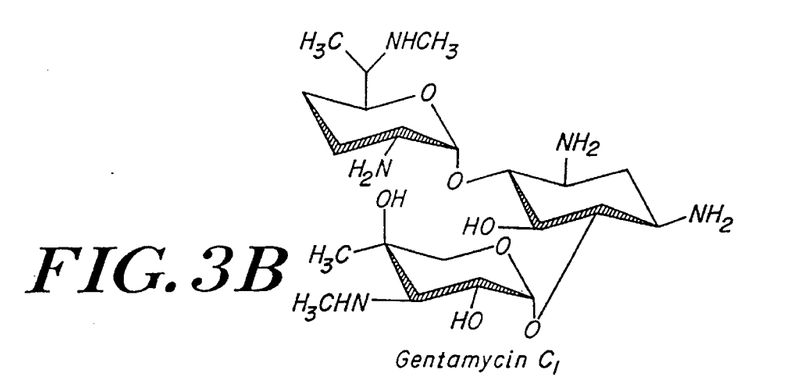
FIG. 3B is a diagrammatic representation of the antibiotic gentamicin $C_1$.
Figure 3C:
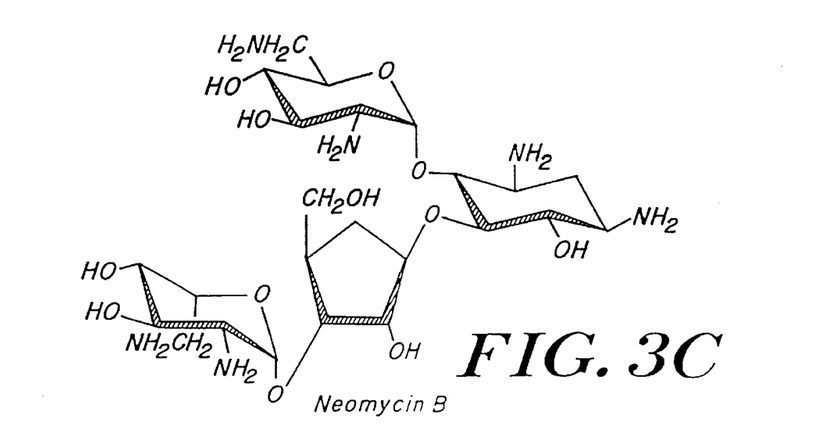
FIG. 3C is a diagrammatic representation of the antibiotic neomycin B.

The screening method of the invention is depicted diagrammatically in FIG. 2. The fluorescently-labelled antibiotic is bound to a preselected region of the target RNA. Contact of the RNA and the antibiotic and binding may occur in solution, such as in a container (e.g., a test tube, dish, or a well of a microtiter plate). Alternatively, the fluorescent antibiotic or the RNA may be dried down onto the wall of a container, and the RNA or antibiotic, respectively, added in solution thereto. The RNA instead may be adhered to a solid support such as an affinity gel, matrix, or column, using methods known in the art (see, e.g., the exemplification). However, the region of the RNA to which the antibiotic binds must not be conformationally hindered by the binding to the support. The support-bound antibiotic is then mixed with the labelled antibiotic in solution.

When the antibiotic is bound to the RNA, it forms a complex which is less fluorescent than the uncomplexed fluorescent antibiotic. Preferably, the fluorescence of the antibiotic is quenched when the antibiotic is bound to the RNA such that fluorescence is detectible only when the antibiotic is uncomplexed. Fluorescence intensity and wavelength measurements are obtained with a fluorescence spectrophotometer.

Alternatively, the complexed antibiotic may emit light that is polarized to a greater degree than the light emitted from the uncomplexed antibiotic. Fluorescence depolarization is a technique in which a fluorophore, such as pyrene, is excited with polarized light. The fluorescence emitted will be polarized to a degree that is inversely related to the amount of Brownian motion which occurs between the interval of light absorption and emission (Guilbautt (1973) *Practical Fluorescence-Theory, Methods and Technique,* Marcel Dekker, Inc. NY, pp. 468–485). The amount of polarization is then a measure of the size of the molecule to which the fluorescence probe is bound. In solution, the fluorophores (such as PYT), will be rapidly moving and rotating, and thus little or no polarization of fluorescence will be observed. On the other hand, if the fluorescently labelled antibiotic is bound to a large molecule of RNA, then the complex will be rotating and moving relatively slowly in solution. The fluorophore will emit polarized light because it is now bound to a larger structure which is not tumbling very rapidly in solution. This technique is particularly useful in cases where fluorescence intensity change might not be observable. The degree of polarization is measured by standard methods, such as with a commercially available fluorimeter having polarizing filters.

The complex is then mixed with a compound-to-be-tested. The compounds-to-be-tested can be antibiotics or other small molecules such as peptides, aminosugars, sugars, polyamines, or aromatic amines.

The fluorescence of the antibiotic in the mixture is then measured. If the compound is able to bind more strongly or with greater specificity or affinity to the preselected region of the target RNA, or if the compound which binds the RNA is present in a higher concentration than the labelled antibiotic, the labelled antibiotic will be displaced from complex and will regain (or increase) its level of fluorescence or will emit fluorescence with less polarity than did the complex. Alternatively and/or additionally, if the compound binds with an affinity or specificity similar to that of the antibiotic, but is present at a high concentration, it will displace the antibiotic in the complex and bind the RNA. Preferably, the fluorescence of the antibiotic is completely restored or is unpolarized when the antibiotic is released from the complex by a competing compound.

The screening method of the invention is illustrated by a method of identifying compounds which inhibit HIV replication. It is known that the TAR region of HIV RNA is required for viral replication, and that this region must bind and interact with cellular proteins for viral replication to occur (Gait and Karn (1993) *Trends Biochem. Sci.* 18: 255–259). Thus, if this region is blocked with an RNA binding molecule specific for this region, viral replication is inhibited. The aminoglycoside antibiotics neomycin B, tobramycin, and lividomycin A are known to inhibit the binding of Rev, a viral regulatory protein required for viral gene expression, to the TAR region of HIV RNA, and in doing so, inhibits HIV replication (Zapp et al. (1993) *Cell* 74: 969–978).

In the method of the invention, the TAR or RRE region of an HIV RNA is bound to a fluorescently-labelled aminoglycoside antibiotic, thereby forming a non-fluorescent complex. The complex is then mixed with a compound-to-be-tested, and the presence of fluorescence detected or the degree of polarization of the fluorescence emitted measured, as described above. The concentration of the compound can be determined with a fluorescence standard curve depicting the fluorescence of the labelled antibiotic mixed as an RNA/antibiotic complex with varying known concentrations of competing unlabelled antibiotic. This method allows for the large scale screening of many new compounds from diversity libraries and other sources. The screen allows for the quantitative measurement of the ability of diverse molecules to bind to the selected regions of RNA.

The present invention is also embodied as a clinical assay or method for determining the presence and serum level of an aminoglycoside antibiotic in a subject. Aminoglycoside antibiotics, such as neomycin, gentamicin and tobramycin, are routinely assayed for their serum levels when administered to patients, as these antibiotics are themselves toxic to the kidney and to hearing (ototoxicity). The present assay system is useful to monitor such serum aminoglycoside levels.

In this assay, a complex is provided which comprises a fluorescent derivative of the antibiotic with which the patient is being treated, and an RNA to which the antibiotic has specifically bound. The RNA may comprise any selected sequence or region which is known to bind an aminoglycoside antibiotic, such as, but not limited to, the RRE or TAR regions of HIV RNA, a decoding region of bacterial ribosomal 16S RNA, a Gram-negative bacterial RNA, or RNA containing SEQ ID NO:8 or 9. The antibiotic in the complex and bound to the RNA is no longer fluorescent. Alternatively, the antibiotic in the complex emits polarized light in comparison to uncomplexed, fluorescently labelled antibiotic. A serum or blood sample is taken from the patient and put in contact with the complex. It may be desirable to add ribonuclease inhibitor to the sample or to the mixture of the sample and the complex to prevent degradation of the RNA. The fluorescence of the labelled antibiotic is then measured, fluorescence being detected if the labelled antibiotic in the complex is displaced by unlabelled antibiotic which has bound to the RNA. Alternatively, the polarity of the fluorescence emitted is measured, the fluorescence being less or unpolarized if the labelled antibiotic is uncomplexed.

The present invention also provides a kit for performing the clinical assay described above, comprising the fluorescently labelled antibiotic complexed with the RNA, and a ribonuclease inhibitor to protect the RNA from degradation by serum enzymes. Other related kits include a DNA which encodes RNA that specifically binds the antibiotic, a reverse transcriptase and ribonucleosides with which to reverse transcribe the RNA, and a fluorescently labelled derivative of the antibiotic with which the patient is being treated. Yet other kits include the target RNA, a competing aminoglycoside antibiotic which has been fluorescently labelled, the fluorescence being quenched when the antibiotic binds the RNA, and the antibiotic in an uncomplexed and unlabelled form for preparing a standard fluorescence curve. The DNA or RNA in the kit may be synthesized or isolated from natural sources. The reverse transcriptase and ribonucleosides are commercially available from a number of sources, including Sigma Chemical Co., St. Louis, Mo. Some kits may also include a ribonuclease inhibitor, such as diethyl pyrocarbonate, which is commercially available, for example, from Fluka (Ronkonkoma, N.Y.).

The present invention is also embodied as a kit for screening for compounds which bind a target bacterial or viral RNA. This kit comprises the target RNA and the fluorescently labelled antibiotic. Any bacterial or viral target RNA and any antibiotic may be included in the kit of the invention, so long as the RNA is able to be selectively bound by the fluorescently labelled antibiotic. For example, the target RNA may be an HIV RNA including the TAR or RRE regions. In other non-limiting examples, the target RNA is a decoding region of a bacterial ribosome or is a Gram-negative or a Gram-positive bacterial RNA. The antibiotic may be an aminoglycoside antibiotic such as tobramycin, neomycin, or gentamicin, or derivatives thereof which may be labelled with any fluorescent label that does not interfere with the binding of the antibiotic to the RNA. Useful labels include, but are not limited to, pyrene, and derivatives thereof.

Because RNA is less stable than DNA, the kit of the invention may alternatively contain a reverse transcriptase and a DNA encoding, and capable of being reversed transcribed to, the target RNA, in place of the target RNA. To use the kit, the DNA is reverse transcribed to the target RNA, which is then mixed with the labelled antibiotic, as described in the methods above.

A kit for diagnosing the presence of HIV in a sample is also provided by the invention. This kit contains a fluorescently labelled antibiotic which is known to bind HIV RNA, and a container in which a sample to be tested is mixed with the antibiotic. Some useful antibiotics, such as tobramycin and its derivatives, belong to the aminoglycoside family.

The invention also provides kits for diagnosing the presence of a bacteria and/or virus in a sample. In such kits are a plurality of different, fluorescently labelled antibiotics, each binding a different bacterial and/or viral RNA. The kits may further include a multiwell container such as a microtiter plate into which a number of different antibiotics or concentrations of antibiotic are placed. The sample may be a biological sample from a subject, such as a serum, blood, or tissue sample, or may be a solution prepared for commercial, investigational, or other use whose purity must be tested.

To address the nature of the interaction between antibiotics and their targets, RNA diversity libraries (Ellington et al. (1990) *Nature* 346: 818–822; Tuerk et al. (1990) *Science* 249: 505–510; and Beaudry et al. (1992) *Science* 257: 635–641) directed against small molecules were used to define the kinds of RNA molecules that bind to a particular aminoglycoside antibiotic. One such aminoglycoside, tobramycin (FIG. 1A), and its derivatives or analogs 6'-N-acetyl tobramycin (FIG. 1B), and 6'-N-4-pyrenebutyryl tobramycin (PYT) (FIG. 1C), were used in this study. This drug is suited to these studies because it has already been shown to inhibit intron splicing (von Ahsen et al. (1991) *Nature (London)* 353: 368–370), and it can be chemically modified specifically at its primary amino group while still retaining biological activity (LeGoffic et al. (1979) *Eur. J. Biochem.* 102: 73–81). This latter issue is important because tobramycin needs to be chemically modified as a consequence of linking it to the affinity column. In addition, the fluorescent and radioactive analogs used here, PYT and $^3$H-acetyl tobramycin respectively, also involve chemical modification at the less hindered 6'-primary amino group of tobramycin (Tangy et al. (1983) *Eur. J. Biochem.* 131: 581–587; and LeGoffic et al. (1979) *Eur. J. Biochem.* 102: 73–81). Moreover, where tested these analogs are still biologically active (LeGoffic et al. (1979) *Eur. J. Biochem.* 102: 73–81).

Initial studies were focused on the interaction of a random RNA diversity pool with a tobramycin affinity column used to select RNA molecules which bind to immobilized tobramycin. This column was prepared using 20 µmoles tobramycin to couple to 15 µmoles N-hydroxysuccinimide reactive sites/ml on the column. This "low stringency" column was used in the initial selections to obtain as many sequences as possible capable of recognizing tobramycin. The randomized pool consisted of 109mer RNA transcripts containing 60 central randomized bases flanked by PCR primer sequences containing a T7 RNA polymerase promoter. The overall design was identical to a published RNA aptamer construct (Famulok et al. (1992) *J. Am. Chem. Soc.* 114: 3990–3991). The original $^{32}$P-labelled-RNA pool was produced by transcription of 120 µg of the DNA pool.

Figure 4:
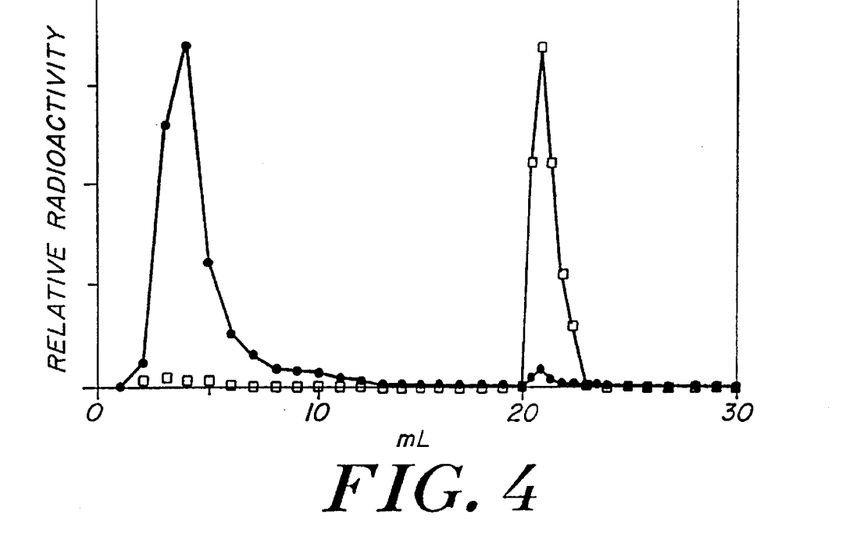
FIG. 4 is a graphic representation of the elution profiles for cycle 2 (♦) and cycle 6 (□) of the RNA selection protocol.

Elution patterns of the RNA from the columns are shown in FIG. 4 for the second and sixth selections. Over 6 cycles of selection, the percentages of RNA specifically eluted with tobramycin were <0.1%, 3.0%, 2.9%, 26%, 55%, and 82%. Further selections did not increase the specific binding pool. The RNA pool transcribed from DNA after the sixth selection could not be eluted from the affinity column, even after 100 column volumes of selection buffer. Furthermore, 10 column volumes of selection buffer containing 50 mM D-glucosamine also did not cause any bound RNA to be eluted from the column, while 96% of the RNA could be eluted with 3 column volumes of 10 mM tobramycin. The observation that D-glucosamine did not cause the elution of the bound RNA suggests that the binding interaction is specific in nature.

The DNA from the random RNA diversity pool was cloned in order to analyze individual sequences. Plasmid DNA from 40 clones was purified, and eighteen of these were sequenced to determine if they included any consensus sequences. No two of the sequences were identical, and no obvious consensus sequences were observed. Ten RNA aptamers were prepared from these clones. These RNAs bound specifically to the affinity column, as they could not be eluted with more than 100 column volumes of selection buffer, but were eluted with 3 columns of selection buffer containing 10 mM tobramycin.

One of these RNAs, clone W13 (SEQ ID NO:1) was chosen for quantitative studies to determine the specificity of its binding to RNA. Using equilibrium dialysis, the $K_D$ for $^3$H-acetyl tobramycin was determined to be 1.3 µM. The dissociation constant for tobramycin was determined to be 3 µM by competition studies with $^3$H-acetyl tobramycin. These values are close to those measured for tobramycin and $^3$H-acetyl tobramycin binding to ribosomal targets (LeGoffic et al. (1979) *Eur. J. Biochem.* 102: 73–81).

Figure 5:
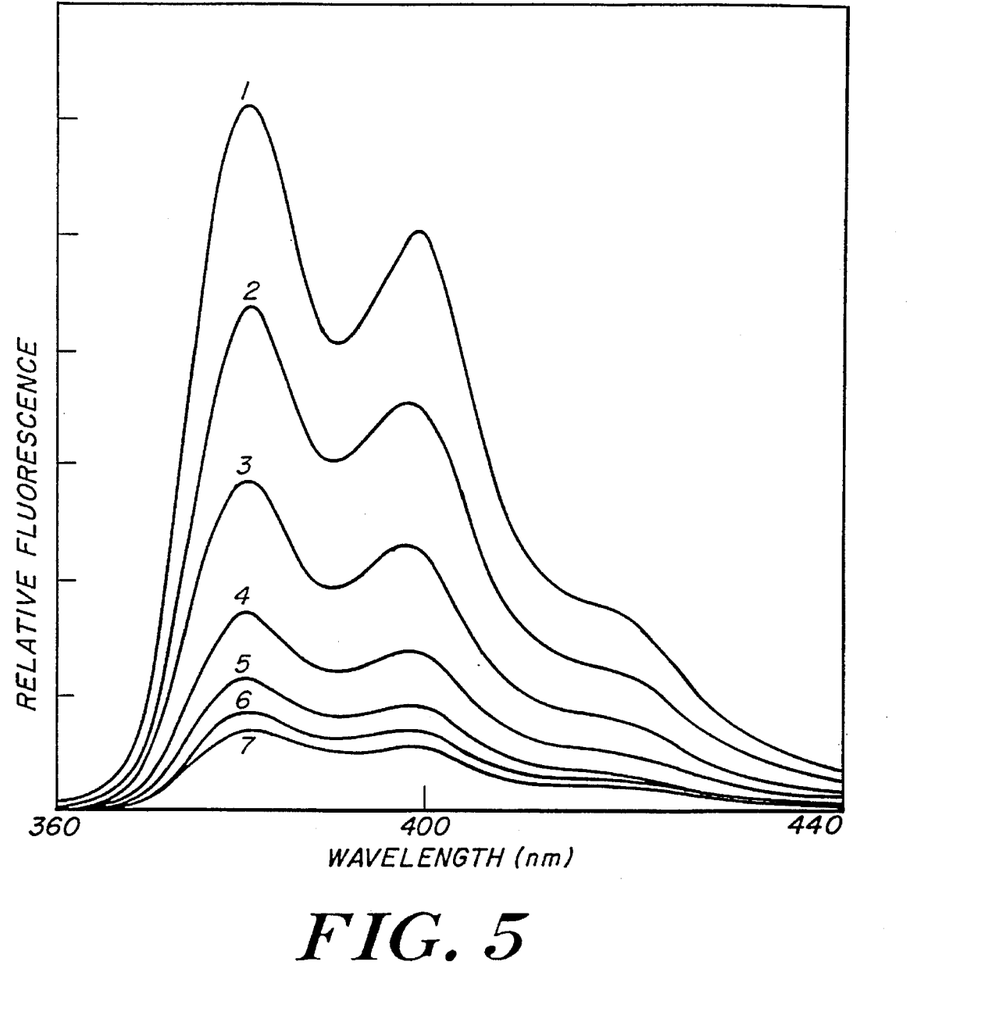
FIG. 5 is a graphic representation of the fluorescence emission spectra of a 151 nM PYT solution in the presence of varying concentrations of W13 RNA: 1) 0; 2) 0.056 µM; 3) 0.112 µM; 4) 0.224 µM; 5) 0.440 µM; 6) 0.700 µM; or 7) 1.100 µM; used for the preparation of a standard fluorescence curve.
Figure 6:
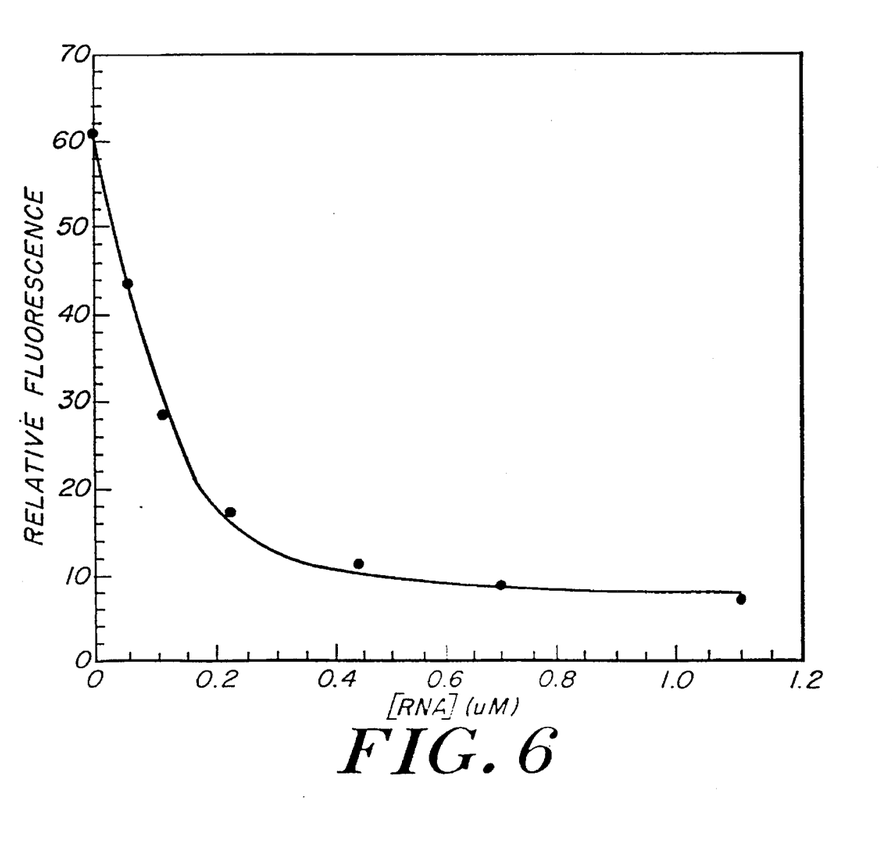
FIG. 6 is a graphic representation of the fluorescence titration of PYT as a function of the concentration of W13 RNA having SEQ ID NO:1, wherein the solid line is calculated (curve obtained by curve fitting using Equation 1 as described in the exemplification)
Figure 7:
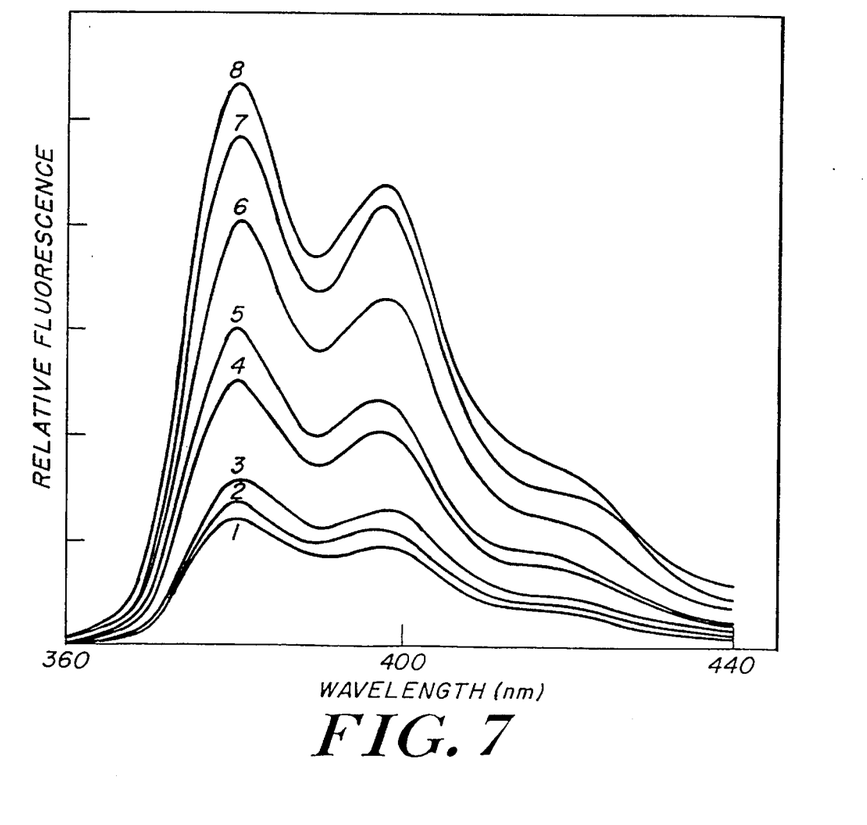
FIG. 7 is a graphic representation of the fluorescence emission spectra of a 152 nM PYT solution containing 300 nM of W13 RNA having SEQ ID NO:1 in the presence of varying concentrations of tobramycin: (1) 0; (2) 0.73 µM; (3) 2.57 µM; (4) 10.06 µM; (5) 44.86 µM; (6) 81.39 µM; (7) 264.85 µM; (8) 631.76 µM.
Figure 8:
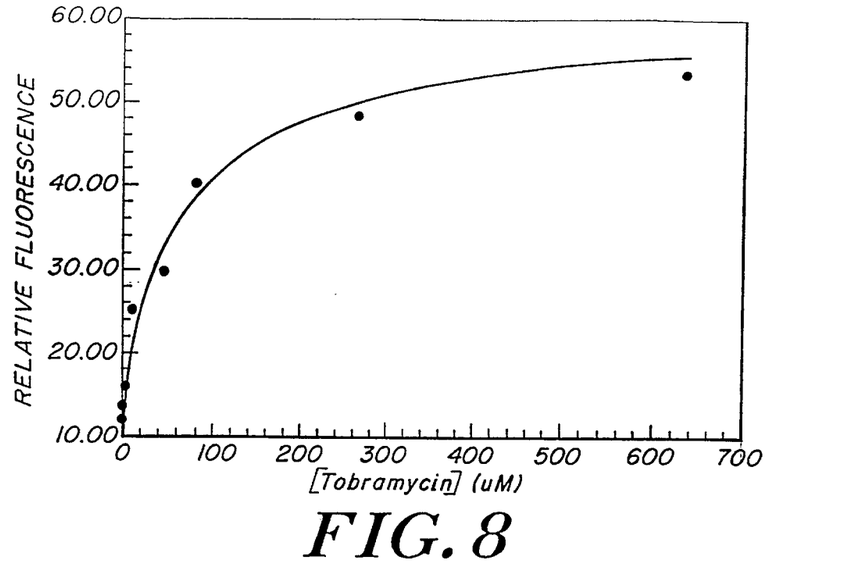
FIG. 8 is a graphic representation of the fluorescence titration of a PYT solution containing W13 RNA having SEQ ID NO:1 as a function of tobramycin concentration, wherein the solid line is calculated (curve obtained by curve fitting) using Equation 2 as described in exemplification.

To study the binding behavior of clone W13, a fluorescently labelled pyrene-conjugated tobramycin derivative "PYT" was prepared. Pyrene derivatives are quite useful for studying RNA interactions, as the fluorescence intensity can be markedly affected by binding to RNA (Kierzek et al. (1993) *J. Am. Chem. Soc.* 115: 4985–4992; and Bevilacqua et al. (1994) *Biochem.* 33: 11340–11348). In the present case, the fluorescence emission intensity of PYT proved to be markedly quenched upon the addition of W13 RNA (FIG. 5), indicating complex formation between the RNA and the ligand. The large dynamic range (>10) observed here makes careful quantitative studies on binding possible. The fluorescence intensity of PYT as a function of RNA concentration fitted an equation for a 1:1 complex (see exemplification), as shown in FIG. 6, giving a $K_D$=20±4 nM. Thus, there is a tight 1:1 complex formed between the antibiotic and RNA. Competition experiments show that tobramycin competes with PYT for binding to the RNA (FIG. 7). Curve fitting using the fluorescence intensity of PYT as a function of the tobramycin concentration gave $K_D$=4.3±0.7 µM for tobramycin (FIG. 8). Therefore, PYT binds to W13 RNA more than 200 times more tightly than does tobramycin itself.

Other antibiotics and D-glucosamine were also tested for their abilities to bind specifically to W13 RNA. The result are shown in Table 1.

TABLE 1

| Antibiotic | $K_D$ (µM) |
|---|---|
| PYT | 0.020 ± .007 |
| tobramycin | 4.3 ± 0.7 |
| D-glucosamine | N.B. |
| erythromycin | 505 ± 25 |
| gentamicin | 4.7 ± 04 |

N.B. = no measurable binding

The fluorescence assay described in the exemplification enables direct measurement of the competition of various ligands for the aminoglycoside binding-site. Tobramycin itself competed, and its $K_D$ was measured to be 4.3 µM, a value close to that measured by the equilibrium dialysis technique. Glucosamine did not measurably compete with PYT binding, showing that simple non-specific binding to charged amino sugars is not the basis for the observed binding. Erythromycin (FIG. 2A), an antibiotic structurally dissimilar from tobramycin, only weakly inhibited PYT binding. By contrast, the two structurally related aminoglycosides gentamicin C (FIG. 2B) and neomycin B (FIG. 2C) proved to be potent inhibitors of binding. Interestingly, both gentamicin and neomycin inhibit the splicing of group I introns about as efficiently as tobramycin itself does (von Ahsen et al. (1991) *Nature (London)* 353: 368–370). In addition, both of these drugs also blocked the binding of acetyl tobramycin to *E. coli* ribosomes (LeGoffic et al. (1979) *Eur. J. Biochem.* 102: 73–81). Thus it appears that similar structural features in RNA are recognized by tobramycin, gentamicin, and neomycin.

To determine whether the W13 RNA clone is representative of the average binding capacity of the random selected RNA pool, the average $K_D$ values for the random selected pool were measured. Using the fluorescence assay described in the exemplification below, it was also determined that overall the selected pool mixture binds PYT with a $K_D$ of 52±8 nM, and binds tobramycin with a $K_D$ of 8.8±0.3 µM. Therefore, the W13 RNA is representative of the average binding capacity of the random selected pool.

To determine whether there are RNAs in the pool which have higher affinity (than in the µM range) for tobramycin, a new affinity column was prepared using 0.075 µmoles tobramycin/ml of Affi-gel (Bio Rad, Hercules, Calif.) in the coupling reaction rather than 20 µmoles tobramycin/ml of gel. The previously selected RNA pool was reselected against this new gel. In over 7 cycles of selection, the percentages of RNA specifically eluted with tobramycin were 0.3%, 4.9%, 6.6%, 21.9%, 9.1%, 50.7%, and 86.1%, for a total amplification of approximately $1.2 \times 10^7$. When this selected pool of RNA was cloned and approximately 40 of the clones were sequenced, two clear consensus sequences, shown below in Table 2 (in bold print), were observed.

TABLE 2

5'... CUGGUUAGUUUUGCACAGUGGUCGAUGCUAGACUUGGUUUAGGUAAU
GAGUCCAAUAGUC...3' (SEQ ID NO:2)
(clones X1, J4, J8, and G6)

5'... GCGGUUGAGCGCUCCGGUACAUUGACAGGCAGGCAUGGUUUAACUAA
UGUGCUUGGACUUGAC...3' (SEQ ID NO:3)
(clones X8 and K9)

5'... CUUGGUUUAGGUAAUGAGCAUCAUCGGCCGAUUUCAUCUCUGUGGGU
AGUACGGAAGCAC...3' (SEQ ID NO:4)
(clones K13)

5'... AGUAUAGCGAGGUUUAGCUACACUCGUGCUGAUCGUUUGGUACGGGA
CCUGCGUGUAGCC...3' (SEQ ID NO:5)
(clones J6, J7, J9, J11, J12, J13, G3, G4, G7, G9, K1, K10, and K12)

5'... CCAAAAAAGUAAGGACGAGAGCCGACUAGGUUUAGCUACACUAGAGC
UCUCCGCCAACGG...3' (SEQ ID NO:6)
(clones J14 and K11)

5'... UGGUUGUCUUGUACGUUCACUGUUACGAUUGUGUUAGGUUUAACUAC
ACUUUGCAAUCG...3' (SEQ IN NO:7)
(clones X3, J2, J3, J10, and G8, X4, K2, K3)

The consensus sequences fall into two groups, UGGU-UUANNUAAUG (SEQ ID NO:8) as seen in SEQ ID NOS:2–4, and AGGUUUANCUACACU (SEQ ID NO:9) as seen in SEQ ID NOS:5–7. Interestingly, the two groups show substantial homology. Also a substantial repetition in sequence is observed. This shows that there are only a few solutions to generating high affinity binding RNA molecules directed towards tobramycin. Furthermore, this result is also consistent with expectations based on the amplification factors observed in the two selections.

Secondary structure analysis using the computer program MFOLD (Jaeger et al. (1989) *Meth. Enzymol.* 183: 281–306) indicated that the consensus sequences in these two constructs were located in stem-loop regions. While there are two different consensus sequences observed, they do show homology. In fact the X1 and J6 stem-loop structures can be drawn to give similar loops including the sequence having SEQ ID NO:8, where N is a any nucleotide.

The binding of tobramycin to two cloned RNAs X1 (SEQ ID NO:2) and J6 (SEQ ID NO:5), representative of both classes of consensus sequences, was measured using the fluorescence techniques described in the exemplification. The results are shown in Table 3.

TABLE 3

| | | Binding Measurements | | |
| | SEQ ID | Dissociation Constants | | |
| RNA | NO: | $K_{1(PYT)}$ | $K_{1(TOB)}$ | $K_{2(TOB)}$ |
|---|---|---|---|---|
| J6 | 5 | $5.38 \pm 0.46^a$ | $2 \pm 1$ | $6.0 \pm 0.4$ |
| X1 | 3 | $7.63 \pm 1.1a$ | $3 \pm 1$ | $15.9 \pm 0.7$ |
| J6a1* | 5 | $286 \pm 10^a$ | $9 \pm 3$ | $2.7 \pm 0.3$ |
| X1s1* | 3 | $65.1 \pm 7.4^b$ | $12 \pm 5$ | $13.2 \pm 0.5$ |

Figure 9:
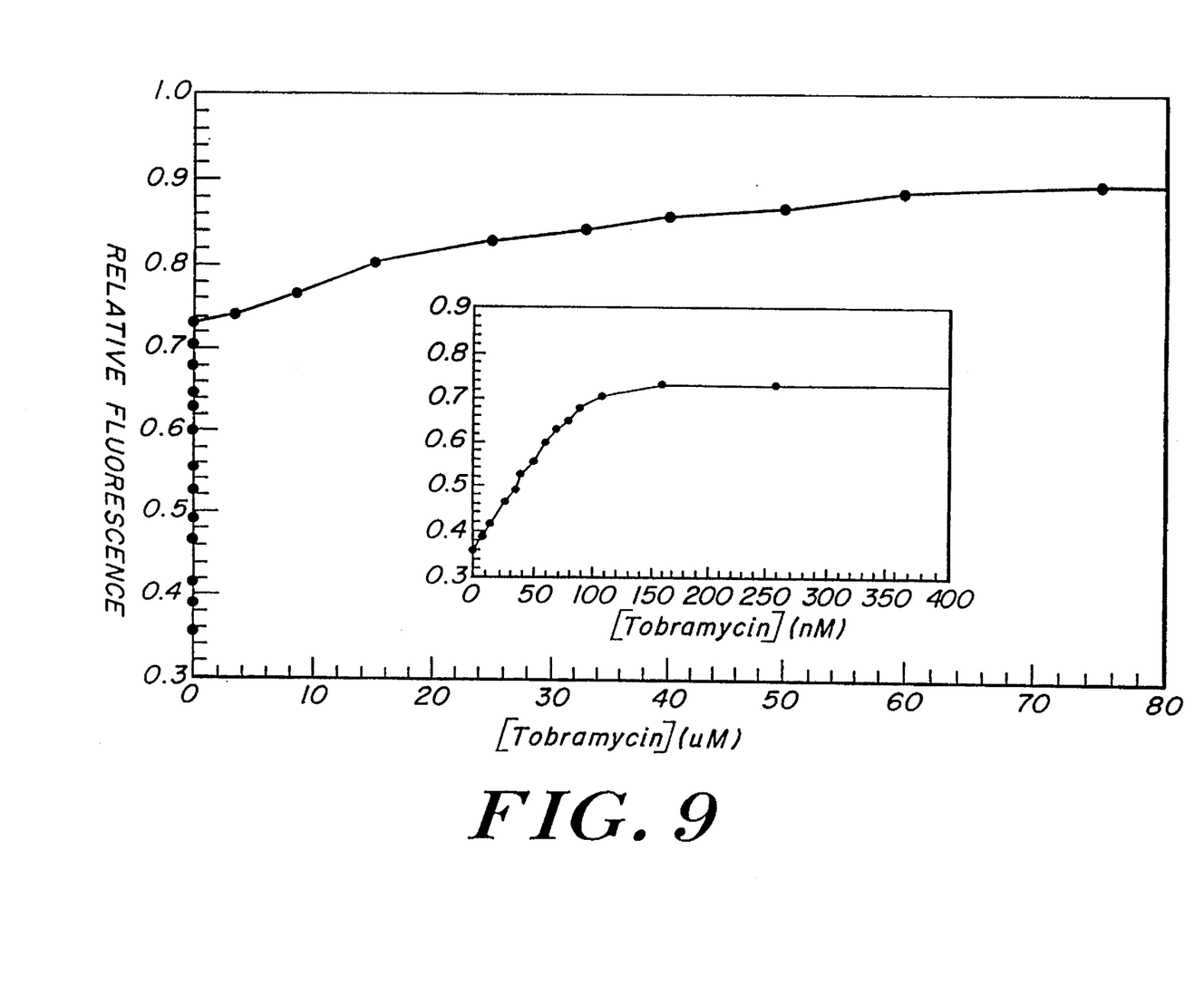
FIG. 9 is a graphic representation of the fluorescence titration of 15 nM PYT solution containing 35 nM J6 RNA having SEQ ID NO:5 as a function of tobramycin concentration; wherein the insert shows the tight (high affinity) binding of tobramycin to this RNA in greater detail.

$K_1$ - high affinity
$K_2$ - low affinity
PYT - 6'-N-4-pyrenebutyryl tobramycin
TOB - tobramycin
$^a$PYT
$^b$6'N-4-pyreneacetyl tobramycin
*synthetically derived from the predicted structures The high affinity binding of PYT to X1 and J6 is shown along with binding data for tobramycin. The binding of tobramycin to both X1 and J6 RNAs was of high affinity. However, molecules of tobramycin specifically bind to each RNA in high affinity and low affinity modes. A saturation binding curve showing the biphasic binding behavior J6 RNA is shown in FIG. 9. The high affinity component binds tobramycin $10^3$ times more tightly than do sensitive ribosomes (LeGoffic et al. (1979) *Eur. J. Biochem.* 102: 73–81).

The above-described experiments show that specific aminoglycoside-binding RNA molecules can be readily selected for, and that the consensus regions on the RNA molecules recognized by tobramycin are confined to specific stem-loops. These studies have enabled the development of screens for molecules other than tobramycin that bind specific regions of, or conformations within, a target RNA.

Zapp et al. (*Cell* (1993) 74: 969–978) showed that HIV replication can be inhibited with aminoglycosides neomycin B, tobramycin, and lividomycin A. They used gel shift experiments to demonstrate the binding of these antibiotics to RNA, and have suggested that aminoglycoside binding to the RRE region of HIV RNA interrupts Rev binding to this region, thereby interfering with HIV replication.

In order to quantitatively determine whether fluorescently labelled tobramycin and other antibiotics bind directly to the RRE region and/or to other regions of the HIV RNA, and with what affinity, the RRE and TAR regions of HIV RNA were prepared and used in the method of the invention as target RNAs. The results are shown in Table 4, below.

TABLE 4

| | Dissociation Constant ($K_D$) | |
| Antibiotic | RRE RNA | TAR RNA |
|---|---|---|
| tobramycin | $2.32 \pm 0.28$ μM | $19.1 \pm 1.1$ μM |
| PYT-1 | $43.9 \pm 6.1$ nM | $51.3 \pm 3.1$ nM |
| neomycin-B | $0.419 \pm 0.0038$ μM | |
| lividomycin-A | $11.9 \pm 0.33$ μM | |
| gentamicin-C | $10.8 \pm 0.68$ μM | |

These studies show that tobramycin, as well as neomycin-B, lividomycin-A, and gentamicin-C bind to both of these target RNAs. The binding of PYT was specific and could be competitvely relieved by tobramycin, neomycin-B, lividomycin-A, and gentamicin-C. These also studies demonstrate that tobramycin to which a pyrene-acetyl moiety has been covalently attached binds more tightly to these target RNAs than does unmodified antibiotic. In addition, unlike gel shift studies, these studies are quantitative; they distinguish the varying degrees of strength with which the different antiboitcs bind. Furthermore, these studies are very sensitive in comparsion to gel shift studies, as evidenced by the ability of these studies to detect antibiotic binding to the TAR region of HIV RNA.

The following examples illustrate the preferred modes of making and practicing the present invention, but are not meant to limit the scope of the invention, since alternative methods may be utilized to obtain similar results.

EXAMPLES

1. Syntheses of Derivatized Antibiotic

A. 6-N-$^3$H-Acetyl Tobramycin

Radiolabelled acetyl tobramycin (Fluka, Ronkonkoma, N.Y.) was prepared essentially according to LeGoffic et al. (*Eur. J. Biochem.* (1979) 102: 73–81) using $^3$H-acetic anhydride (American Radiolabeled Chemicals, St. Louis, Mo.), but was purified by ion exchange chromatography (see synthesis of PYT for details of ion exchange methods) rather than by preparative thin layer chromatography. The $R_f$ was 0.62 on silica (NH$_4$OH:methanol:n-butanol=5:4:3). MS (FAB)=510/(M+H)+.

B. 6'-N-4-Pyrenebutyryl Tobramycin (PYT)

1.0 g (3.5 mmol) 1-pyrenebutyric acid (Fluka, Ronkonkoma, N.Y.) and 0.40 g (3.5 mmol) N-hydroxysuccinimide (Fluka, Ronkonkoma, N.Y.) were dissolved in 40 ml dioxane. To this solution was added 0.72 g (3.5 mmol) N,N-dicyclohexylcarbodiimide (DCC) (Fluka, Ronkonkoma, N.Y.). After reaction at room temperature for 4 hr, the N-hydroxysuccinimide ester of 1-pyrenebutyric acid (PYS) product was purified by repeated recrystallization from isopropanol. Final yield was 0.87 g (65%). (TLC (silica):Rf=0.56 (CHCl$_3$:MeOH=20:1). MS (EI): 385/M+.) 100 mg (0.21 mmol) tobramycin and 81 mg PYS (0.21 mmol) were dissolved in 1.5 ml N,N-dimethylformamide (DMF) (Fluka, Ronkonkoma, N.Y.), and a small amount of H$_2$O was added to fully dissolve tobramycin. After reacting at room temperature for 1 hr, the reaction mixture was diluted with 20 ml H$_2$O, filtered, and applied to an Amberlit CG-50 column (5×120 mm) (Sigma Chemical Co., St. Louis, Mo.). The column was washed with 50 ml H$_2$O, 50 ml 0.1M NH$_4$OH, and finally 0.25M NH$_4$OH; the final elution gave the pure PYT, 40 mg (yield=26%). TLC (silica): $R_f$=0.62 (H$_2$O:methanol:n-butanol:NH$_4$OH= 5:4:3:1). MS (FAB):738/(M+H)+. The synthesis of 6'-N-4-pyreneacetyl tobramycin was carried out identically to the synthesis of PYT except for the substitution of 1-pyreneacetic acid (Fluka, Ronkonkoma, N.Y.) for 1-pyrenebutyric acid.

2. Affinity Column Preparation

An N-hydroxysuccinimide Affi-Gel affinity column (Bio-Rad, Hercules, Calif.) was derivatized with either 20 μmoles or 0.075 μmoles tobramycin per ml of gel to generate the affinity columns. Excess N-hydroxysuccinimide linkages were blocked by adding 1M ethanolamine. The resulting column served as the support for the RNA selections. The tobramycin concentration on column was estimated as about 15 mM. Selections were performed in 1 ml column volumes in a buffer (selection buffer) containing 140 mM NaCl, 5 mM KCl, 1 mM CaCl$_2$, 1 mM MgCl$_2$, and 20 mM Tris acetate, pH 7.4 (Bock et al. (1992) *Nature* 355: 564–566). A 1 ml Affi-Gel 10 pre-column treated with ethanolamine was used in all selections.

3. Preparation of Nucleic Acid Pools and Selections With Tobramycin

The original double stranded DNA pool was constructed by large scale PCR amplification of the synthesized 109mer random DNA pool (Oligos, Etc., Inc., Wilsonville, Oreg.) containing 60 random nucleotides. 60 μg of the synthesized 60mer ($10^9$ nucleotides including primers (Oligos, Etc., Inc., Wilsonville, Oreg.) previously described by Famulok et al. (*J. Am. Chem. Soc.* (1992) 114: 3990–3991), (maximum of about $10^{15}$ individual sequences) were used for a 10 ml scale PCR reaction using the GeneAmp PCR Kit (Perkin Elmer, Norwalk, Conn.). The original RNA pool was constructed by transcription of 120 μg double-stranded DNA. $^{32}$P-labelled RNA prepared with T4 RNA ligase (Romaniuk et al. (1983) *Meth. Enzymol.* 100: 52–59) using $^{32}$P-rATP (New England Nuclear, Boston, Mass.) was used to follow all selections. RNA, purified by Sephadex G-50 (Pharmacia, Piscataway, N.J.) column chromatography to remove unincorporated nucleotides, was heated at 75° C. for 5 min., and then cooled down to room temperature. The RNA was then applied to the pre-column and washed directly onto the tobramycin affinity column with 1 ml of buffer. This was followed by washing with 20 column volumes of the buffer. Specifically bound RNAs were eluted with 3 column volumes of 10 mM tobramycin in the selection buffer. For the first round 1.3 mg of RNA was used; in succeeding rounds 40–60 μg of RNA was used.

The RNA was precipitated with ethanol, with glycogen as carrier. RNA reverse transcription and PCR were performed in a single tube, using a GeneAmp Thermostable rTth Reverse Transcriptase RNA PCR kit (Perkin Elmer, Norwalk, Conn.). About 50 ng of RNA template was used for 20 μl scale reverse transcription reactions. The succeeding PCR reaction was done for only 4–8 thermocycles to ensure high quality of the PCR products. Cloning of PCR DNA products was conducted using a pBluescript II SK(–) phagemid cloning vector (Stratagene, LaJolla, Calif. and a XL1-Blue MRF' *E. coli* (Stratagene, LaJolla, Calif.) as the host bacteria.

4. Binding Studies

For binding studies, different concentrations of RRE RNA (from 0 to 300 nm) were mixed with a constant concentration (15 nM) PYT in Binding buffer (140 mM NaCl, 1 mM MgCl$_2$, 20 mM HEPES, pH 7.4), 2 ml total volume, for 1–5 min. at 20° C. in a semimicro-cell cuvette. The fluorescence was measured on a Perkin-Elmer Model 512 double beam fluorescence spectrophotometer. The excitation wavelength used was 330 nm. The intensities of fluorescence emission at 390 nm were used to calculate dissociation constants. Generally 8 to 12 points were used for calculation.

For competitive binding studies, different concentrations of antibiotic (glucosamine (0–10 mM), erythromycin (0–6 mM), gentamicin C (0–700 μM), or neomycin B (0–650 μM)), were mixed with constant concentrations of RNA (300 nM W13) and PYT (150 nM), in Binding buffer (140 mM NaCl, 5 mM KCl, 1 mM MgCl$_2$, 1 mM CaCl$_2$, 20 mM HEPES, pH 7.4), 750 μl total volume, for 1–5 min. at 20° C. in a semimicro-cell cuvette. The fluorescence was measured on a Perkin-Elmer Model 512 double beam fluorescence spectrophotometer. The excitation wavelength used was 341 nm. The intensities of fluorescence emission at 380 nm were used to calculate dissociation constants. Generally 8 to 10 points were used for calculation.

In other competitive binding studies, TAR or RRE RNA was added at a constant concentration of 100 nM±5% and PYT at 15 nM. Different concentrations of competitive antibiotic (tobramycin (o-60 μM), gentamicin C (0–100 μM), neomycin B (0–4 μM), or lividomycin A (0–100 μM) or Rev protein (0–6 μM) were mixed with constant concentrations of RNA (100 nM TAR or RRE) and C1PYT (15 nM), in Binding buffer (140 mM NaCl, 5 mM KCl, 1 mM MgCl$_2$, 20 mM HEPES, pH 7.4), 2 ml total volume, for 1–5 min. at 20° C. in a semimicrocell cuvette. The fluorescence was measured on a Perkin-Elmer Model 512 double beam fluorescence spectrophotometer. The excitation wavelength used was 330 nm. The intensities of fluorescence emission at 390 nm were used to calculate dissociation constants. Generally 8 to 12 points were used for calculation.

Wild type and mutant RRE RNAs were transcribed in vitro by T7 RNA polymerase using synthetic oligonucleotide templates, as described by Milligan et al. (Meth. Enzymol. (1989) 180: 51–62).

5. Fluorescence Measurements

Steady state fluorescence measurements were performed on a double beam fluorescence spectrometer (Perkin-Elmer Model 512, Norwalk, Conn.). The excitation wavelength was 341 nm. All measurements were done at 20° C. in 140 mM NaCl, 5 mM KCl, 1 mM CaCl$_2$, 1 mM MgCl$_2$, and 20 mM HEPES, pH 7.4. The $K_D$ of the PYT and the RNA aptamer was calculated by the curve fitting of the fluorescence intensity as a function of RNA concentration, using the following equation (assuming a 1:1 complex): $I=I_o+0.5\Delta\epsilon\,([PYT]_o-(([PYT]_o+[RNA]_o KI)^2-4[PYT]_o[RNA]_o)^{0.5})$  (equation 1), where $I_o$ and $I$ are the fluorescence intensities of PYT in the absence and presence of RNA, respectively.

$\Delta\epsilon$ is the difference between the fluorescence intensities of 1 μM PYT in the presence of an infinite concentration of RNA, and in its absence.

$[RNA]_o$ is the total concentration of RNA added.

$[PYT]_o$ is the total concentration of PYT.

Competition binding measurements of antibiotics with RNA and PYT were performed at constant concentrations of PYT and RNA by monitoring fluorescence intensity changes as a function of changing concentrations of the antibiotics (a standard fluorescence curve). The $K_D$s for the antibiotics were calculated by the curve fitting of the fluorescence intensity of PYT as a function of antibiotic concentration, using the following equation:

$I=I_o+\Delta\epsilon[PYT\bullet RNA]$ where $[PYT\bullet RNA]=0.5((([PYT]_o+[RNA]_o)([RNA]_o+K_D)+K_I([T]_o+[RNA]_o+K_D)-((([PYT]_o+[RNA]_o)([RNA]_o+K_D)+K_I([T]_o+[RNA]_o+K_D))^2-4([RNA]_o+K_D)\,[PYT]_o[RNA]_o([RNA]_o+K_D))^{0.5})([RNA]_o+K_D)$  (equation 2)

and $K_D$ and $K_I$ are the dissociation constants for the antibiotic and PYT respectively.

$[T]_o$ is the total concentration of antibiotic added. Measurements were taken at least twice for each measured $K_D$.

6. Equilibrium Dialysis

Equilibrium dialysis measurements were performed according to the procedure of Lorsch et al. (*Biochem.* (1994) 33: 973–982).

EQUIVALENTS

Those skilled in the art will recognize, or be able to ascertain, using no more than routine experimentation, numerous equivalents to the specific substances and procedures described herein. Such equivalents are considered to be within the scope of this invention, and are covered by the following claims.

---

What is claimed is:

1. A method of screening for compounds which bind to a target RNA, the method comprising the steps of:
   (a) measuring the fluorescence of a fluorescently-labelled antibiotic;
   (b) binding the fluorescently-labelled antibiotic to a preselected region of the target RNA, thereby forming a complex which is less fluorescent than the uncomplexed fluorescent antibiotic;
   (c) mixing the complex with a compound-to-be-tested, and;
   (d) measuring the fluorescence of the antibiotic, the antibiotic becoming more fluorescent if the compound displaces the antibiotic in the complex and binds to the preselected region of the target RNA.

2. The method of claim 1 wherein the antibiotic is an aminoglycoside antibiotic.

3. The method of claim 2 wherein the antibiotic is selected from the group consisting of tobramycin, gentamicin, neomycin, and lividomycin.

4. The method of claim 1 wherein the antibiotic is fluorescently labelled with pyrene or a derivative thereof.

5. The method of claim 1 wherein the target RNA is a viral or bacterial RNA.

6. The method of claim 5 wherein the target RNA is an HIV RNA, and the preselected region of HIV RNA comprises the RRE or TAR region.

7. The method of claim 5 wherein the target RNA is a Gram-negative bacterial RNA.

8. The method of claim 5 wherein the target RNA is a decoding region of bacterial ribosomal 16S RNA.

9. The method of claim 1 wherein the fluorescently-labelled antibiotic binds the target RNA with a dissociation constant in the nanomolar to micomolar range.

10. The method of claim 1 wherein the target RNA comprises SEQ ID NO:8.

11. The method of claim 1 wherein the target RNA comprises SEQ ID NO:9.

12. A method of screening for compounds which inhibit HIV replication, the method comprising the steps of:
  (a) binding the TAR or RRE region of an HIV RNA to a fluorescently-labelled antibiotic, thereby forming a non-fluorescent complex,
  (b) mixing the complex with a compound-to-be-tested; and
  (c) detecting the presence of fluorescence, the antibiotic becoming fluorescent again if the compound being tested displaces the antibiotic in the complex and binds the TAR or RRE region of the target RNA,
  the binding of the TAR region or the RRE region by the compound thereby inhibiting the replication of HIV.

13. The method of claim 12 wherein the antibiotic is an aminoglycoside antibiotic.

14. The method of claim 13 wherein the antibiotic is selected from the group consisting of tobramycin, gentamicin, neomycin, and lividomycin.

15. The method of claim 12 wherein the antibiotic is fluorescently labelled with pyrene or a derivative thereof.

16. A method of screening for compounds which bind to a target RNA, the method comprising the steps of:
  (a) measuring the polarization of light emitted from a fluorescently-labelled antibiotic;
  (b) binding the fluorescently-labelled antibiotic to a preselected region of the target RNA, thereby forming a complex which emits light which is more polarized than light emitted from the uncomplexed fluorescent antibiotic;
  (c) mixing the complex with a compound-to-be-tested; and
  (d) measuring the polarization of light emitted from the antibiotic, the emitted light being less polarized than light emitted from the complexed antibiotic if the compound displaces the antibiotic in the complex and binds to the preselected region of the target RNA.

17. A kit for screening for compounds which bind a target bacterial or viral RNA, the kit comprising:
  (a) the target RNA; and
  (b) a fluorescently labelled antibiotic which has the ability to become reversibly non-fluorescent when specifically bound to a preselected region of the target RNA.

18. The kit of claim 17 wherein the antibiotic is an aminoglycoside antibiotic.

19. The kit of claim 18 wherein the antibiotic is selected from the group consisting of tobramycin, gentamicin, neomycin, and lividomycin.

20. The kit of claim 17 wherein the antibiotic is fluorescently labelled with pyrene.

21. A kit for screening for compounds which bind a target bacterial or viral RNA, the kit comprising:
  (a) a DNA which can be reverse transcribed to the target RNA;
  (b) a plurality of ribonucleosides;
  (c) a reverse transcriptase; and
  (d) a fluorescently labelled antibiotic which has the ability to become reversibly non-fluorescent when specifically bound to a preselected region of the target RNA.

22. The kit of claim 24 wherein the antibiotic is fluorescently labelled with pyrene.

* * * * *

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
        ( A ) LENGTH: 60 base pairs
        ( B ) TYPE: nucleic acid
        ( C ) STRANDEDNESS: single
        ( D ) TOPOLOGY: linear     ( i i ) MOLECULE TYPE: RNA (genomic)

( i i i ) HYPOTHETICAL: NO

( i v ) ANTI-SENSE: NO

( x i ) SEQUENCE DESCRIPTION: SEQ ID NO:1:

CGUUUGGGGU CCCACAACAC AGGUCUUUGC UGGUCAUAUA UGCGUGUCCU CUAGGAAGUG    60

( 2 ) INFORMATION FOR SEQ ID NO:2:

( i ) SEQUENCE CHARACTERISTICS:
        ( A ) LENGTH: 60 base pairs
        ( B ) TYPE: nucleic acid
        ( C ) STRANDEDNESS: single
        ( D ) TOPOLOGY: linear     ( i i ) MOLECULE TYPE: RNA (genomic)

(iii) HYPOTHETICAL: NO (iv) ANTI-SENSE: NO (xi) SEQUENCE DESCRIPTION: SEQ ID NO:2:

CUGGUUAGUU UUGCACAGUG GUCGAUGCUA GACUUGGUUU AGGUAAUGAG UCCAAUAGUC    60

(2) INFORMATION FOR SEQ ID NO:3:

(i) SEQUENCE CHARACTERISTICS:
        (A) LENGTH: 63 base pairs
        (B) TYPE: nucleic acid
        (C) STRANDEDNESS: single
        (D) TOPOLOGY: linear     (ii) MOLECULE TYPE: RNA (genomic)

(iii) HYPOTHETICAL: NO

(iv) ANTI-SENSE: NO

(xi) SEQUENCE DESCRIPTION: SEQ ID NO:3:

GCGGUUGAGC GCUCCGGUAC AUUGACAGGC AGGCAUGGUU UAACUAAUGU GCUUGGACUU    60

GAC    63

(2) INFORMATION FOR SEQ ID NO:4:

(i) SEQUENCE CHARACTERISTICS:
        (A) LENGTH: 60 base pairs
        (B) TYPE: nucleic acid
        (C) STRANDEDNESS: single
        (D) TOPOLOGY: linear     (ii) MOLECULE TYPE: RNA (genomic)

(iii) HYPOTHETICAL: NO

(iv) ANTI-SENSE: NO

(xi) SEQUENCE DESCRIPTION: SEQ ID NO:4:

CUUGGUUUAG GUAAUGAGCA UCAUCGGCCG AUUUCAUCUC UGUGGGUAGU ACGGAAGCAC    60

(2) INFORMATION FOR SEQ ID NO:5:

(i) SEQUENCE CHARACTERISTICS:
        (A) LENGTH: 60 base pairs
        (B) TYPE: nucleic acid
        (C) STRANDEDNESS: single
        (D) TOPOLOGY: linear     (ii) MOLECULE TYPE: RNA (genomic)

(iii) HYPOTHETICAL: NO

(iv) ANTI-SENSE: NO

(xi) SEQUENCE DESCRIPTION: SEQ ID NO:5:

AGUAUAGCGA GGUUUAGCUA CACUCGUGCU GAUCGUUUGG UACGGACCU GCGUGUAGCC    60

(2) INFORMATION FOR SEQ ID NO:6:

(i) SEQUENCE CHARACTERISTICS:
        (A) LENGTH: 60 base pairs
        (B) TYPE: nucleic acid
        (C) STRANDEDNESS: single
        (D) TOPOLOGY: linear     (ii) MOLECULE TYPE: RNA (genomic)

(iii) HYPOTHETICAL: NO ( i v ) ANTI-SENSE: NO ( x i ) SEQUENCE DESCRIPTION: SEQ ID NO:6:

CCAAAAAGU AAGGACGAGA GCCGACUAGG UUUAGCUACA CUAGAGCUCU CCGCCAACGG 60

( 2 ) INFORMATION FOR SEQ ID NO:7:

( i ) SEQUENCE CHARACTERISTICS:
        ( A ) LENGTH: 59 base pairs
        ( B ) TYPE: nucleic acid
        ( C ) STRANDEDNESS: single
        ( D ) TOPOLOGY: linear     ( i i ) MOLECULE TYPE: RNA (genomic)

( i i i ) HYPOTHETICAL: NO

( i v ) ANTI-SENSE: NO

( x i ) SEQUENCE DESCRIPTION: SEQ ID NO:7:

UGGUUGUCUU GUACGUUCAC UGUUACGAUU GUGUUAGGUU UAACUACACU UUGCAAUCG 59

( 2 ) INFORMATION FOR SEQ ID NO:8:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear     ( i i ) MOLECULE TYPE: RNA (genomic)

( i i i ) HYPOTHETICAL: NO

( i v ) ANTI-SENSE: NO

( x i ) SEQUENCE DESCRIPTION: SEQ ID NO:8:

UGGUUUANNU AAUG 14

( 2 ) INFORMATION FOR SEQ ID NO:9:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear     ( i i ) MOLECULE TYPE: RNA (genomic)

( i i i ) HYPOTHETICAL: NO

( i v ) ANTI-SENSE: NO

( x i ) SEQUENCE DESCRIPTION: SEQ ID NO:9:

AGGUUUANCU ACACU 15